United States Patent
Maeda

(10) Patent No.: US 9,103,810 B2
(45) Date of Patent: Aug. 11, 2015

(54) SEALING STRUCTURE FOR LIQUID PASSAGE CONNECTION PART

(75) Inventor: Yoshiaki Maeda, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 0 days.

(21) Appl. No.: 13/698,264

(22) PCT Filed: May 17, 2010

(86) PCT No.: PCT/JP2010/058279
§ 371 (c)(1),
(2), (4) Date: Nov. 15, 2012

(87) PCT Pub. No.: WO2011/145162
PCT Pub. Date: Nov. 24, 2011

(65) Prior Publication Data
US 2013/0062836 A1    Mar. 14, 2013

(51) Int. Cl.
*G01N 30/04* (2006.01)
*G01N 30/18* (2006.01)
*G01N 30/24* (2006.01)
*G01N 35/10* (2006.01)

(52) U.S. Cl.
CPC .............. *G01N 30/18* (2013.01); *G01N 30/24* (2013.01); *G01N 35/1079* (2013.01); *G01N 2030/185* (2013.01)

(58) Field of Classification Search
CPC .......... F16L 21/03; F16J 21/03; F16J 15/061; F16J 15/166; F16J 15/121; F16J 15/0887; G01N 30/18; G01N 30/24; G01N 2030/185; G01N 35/1079

USPC .................. 277/625, 630, 637, 638
See application file for complete search history.

(56) References Cited

U.S. PATENT DOCUMENTS 5,209,501 A * 5/1993 Smith .......................... 277/522
7,195,229 B2    3/2007 Maeda

FOREIGN PATENT DOCUMENTS

JP    2003215118 A    7/2003
JP    2008-58064 A    3/2008

OTHER PUBLICATIONS

Japanese language international search report dated Aug. 30, 2010 and its English language translation issued in corresponding PCT application PCT/JP2010/058279.
(Continued)

*Primary Examiner* — Gilbert Lee
(74) *Attorney, Agent, or Firm* — Morgan, Lewis & Bockius LLP

(57) ABSTRACT

When a sealing member held in a cavity of a housing is pressed by a cap toward the bottom of the cavity, the side surface of the sealing member is inclined to laterally expand. As a result, in the opening-side portion of the sealing member, the side surface is strongly pressed on the wall surface of the cavity, causing a strong friction force at the contact surface, which prevents the pressing force applied from the opening side from being transmitted to the bottom side. Therefore, at the beginning of the pressing operation, the internal stress of the sealing member is higher in the opening-side portion than in the bottom-side portion. With the lapse of time from the beginning of the pressing operation, the opening-side portion of the sealing member under the higher internal stress gradually moves toward the bottom side against the friction force.

8 Claims, 2 Drawing Sheets

(56) References Cited

OTHER PUBLICATIONS

Japanese language international preliminary report on patentability dated Dec. 10, 2012 and its English language translation issued in corresponding PCT application PCT/JP2010/058279.

Examination report received for Chinese Patent Application No. 201080066812.6, mailed on Jun. 3, 2014, 8 pages (2 pages of English Translation and 6 pages of Official Copy).

Examination Report Received for Chinese Patent Application No. 201080066812.6, mailed on Jan. 7, 2015, 7 pages (3 pages of English Translation and 4 pages of Official Copy).

* cited by examiner

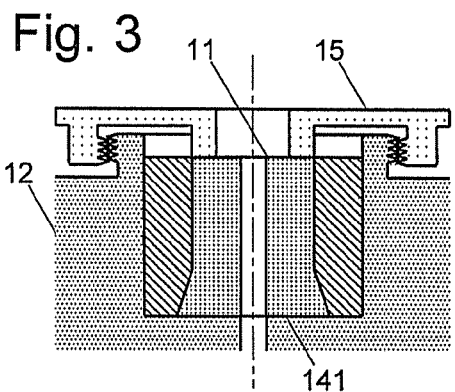
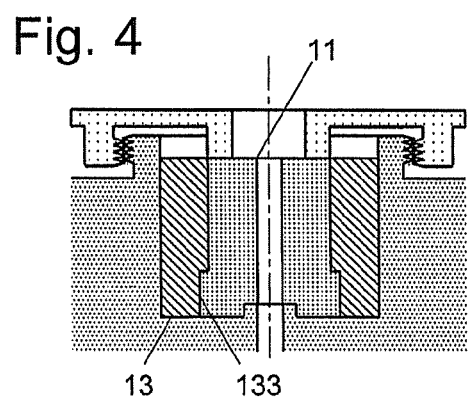
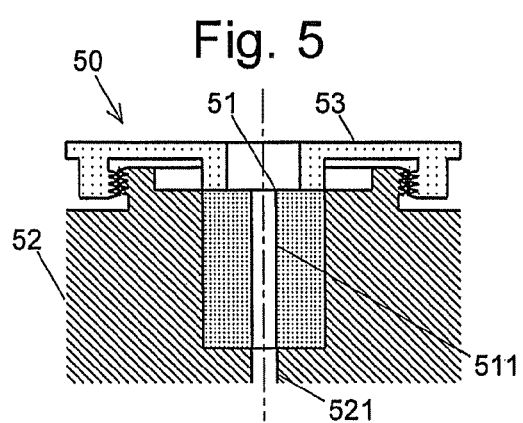
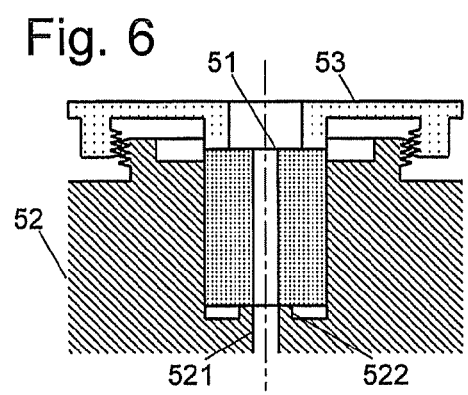

SEALING STRUCTURE FOR LIQUID PASSAGE CONNECTION PART

TECHNICAL FIELD

The present invention relates to a sealing structure for the connection part of a passage through which a liquid sample passes.

BACKGROUND ART

In an analysis using a liquid chromatograph, an auto-sampler is used to automatically introduce a plurality of liquid samples to the column in a predetermined order. One commonly known type of auto-sampler uses a so-called total volume injection method, in which a predetermined amount of sample is collected from a sample bottle and the entire amount of the collected sample is injected into a passage through which a mobile phase is flowing (see Patent Document 1).

In a sample injection process by the total volume injection method, a predetermined amount of sample is suctioned from a sample bottle through a sampling needle and sent into a sample loop (measuring loop) connected to the rear end of the sampling needle. Subsequently, the tip of the sampling needle is connected to a sample injection port, after which a six-way valve located ahead of the sample injection port is operated to create a flow passage which serially connects the mobile phase container, the sample loop, the sampling needle, the sample injection port, the six-way valve and the column in this order. Then, a mobile phase in the mobile phase container is pumped into the flow passage by means of a liquid supply pump, whereby the sample held in the sample loop is flushed away, to be entirely introduced into the column.

In the auto-sampler using the total volume injection method, a high pressure is applied to the mobile phase to shorten the staying time of the sample in the column and thereby reduce the analyzing time. For this purpose, it is necessary to sufficiently seal the connection part of the passage so that it can withstand the high pressure. Particularly, in the sample injection port, it is naturally important to achieve a high level of sealing effect at the connection part of the sampling needle, i.e. the contact area between the sampling needle and a resin-made sealing member having a through-hole communicating with the needle. Furthermore, the sealing on the opposite side of the sealing member, i.e. on the contact surface between the sealing member and a metallic housing having a sample introduction hole communicating with the through-hole of the sealing member, is also important.

FIG. 5 shows a schematic configuration of a conventional sample injection port 50. A resin-made seal member 51 having a through-hole 511 for allowing the passage of a sample is held in a cavity of a metallic housing 52, on which a cap 53 is placed to apply a pressure to the upper side of the seal member 51. This pressure makes the lower surface of the seal member 51 tightly pressed on the bottom surface of the cavity of the housing 52, thus maintaining the sealing effect at the connection between the through-hole 511 of the sealing member 51 and the sample introduction hole 521 of the housing 52.

As shown in FIG. 6, the housing 52 may have a ring-shaped projection 522 formed around the opening of the sample injection hole 521 at the bottom of the cavity. In this case, the lower surface of the sealing member 51 comes in contact with only the upper surface of the projection 522. Since the contact area is smaller, a higher pressure can be applied to the contact surface, whereby the sealing effect at the connection part of the passage can be improved.

BACKGROUND ART DOCUMENT

Patent Document

Patent Document 1: JP-A 2003-215118

SUMMARY OF THE INVENTION

Problem to be Solved by the Invention

When the Resin-Made Sealing Member 51 is Kept Under Pressure for a Long Time, relaxation of the internal stress occurs in the sealing member 51 due to a creep deformation thereof, which decreases the pressure on the contact surface between the sealing member 51 and the housing 52, and deteriorates the sealing property. This problem occurs in the case where the cavity of the housing 52 has a flat bottom surface (as in FIG. 5) as well as the case where a ring-shaped projection 522 is formed at its bottom (as in FIG. 6).

The present invention has been developed in view of this point. Its objective is to provide a sealing structure which can maintain the sealing property at a connection part of a passage even after a long period of use.

Means for Solving the Problems

A sealing structure according to the present invention aimed at solving the aforementioned problem includes:

a) a sealing member having a through-hole for allowing the passage of a sample;

b) a housing having a cavity for holding the sealing member, the cavity having a sample introduction hole at the bottom thereof, the sample introduction hole communicating with the through-hole; and c) a pressure device for pressing the sealing member toward the bottom of the cavity, wherein the cavity is shaped so that the wall surface of the cavity fits with the external shape of the sealing member in the pressure-free state in a portion closer to the opening of the cavity from a predetermined depth thereof while the cavity has a larger cross-section in a portion closer to the bottom of the cavity from the aforementioned depth than in the portion closer to the opening.

Effect of the Invention

In the sealing structure according to the present invention, when the sealing member held in the cavity of the housing is pressed toward the bottom of the cavity by the pressure device, the lower surface of the sealing member is pressed on the bottom of the cavity, with the side surface of the seal member being urged to laterally expand. In the portion closer to the opening of the cavity from a predetermined depth thereof, the wall surface fits with the external shape of the sealing member in the pressure-free state, so that the sealing member cannot laterally expand in this portion. By contrast, in the portion closer to the bottom side from the aforementioned depth, the cavity has a larger cross-section so that the sealing member can laterally expand in this portion.

In the portion closer to the opening, the side surface of the sealing member is strongly pressed on the wall surface of the cavity due the lateral expansion, causing a strong friction on the contact surface, which prevents the pressing force applied from the opening side by the pressure device from being fully transmitted to the bottom side. Therefore, at the beginning of the pressing operation, the internal stress of the sealing member is higher in the opening-side portion than in the bottom-side portion.

With the lapse of time from the beginning of the pressing operation, the opening-side portion of the sealing member under the higher internal stress gradually moves toward the bottom side against the friction force. As a result, the pressure in the opening-side portion is gradually transmitted to the bottom-side portion, increasing the contact pressure between the sealing member and the housing at the bottom of the cavity. By this mechanism, the sealing effect at the connection part of the passage at the bottom is maintained for a long time.

In the bottom-side portion of the sealing member, since the internal stress is low, the stress relaxation barely occurs and the sealing member maintains its elasticity. Accordingly, even if the stress relaxation due to a creep deformation occurs in the opening-side portion of the sealing member, the sealing effect at the connection part of the passage is maintained for a long time due to the elastic force of the bottom-side portion.

If relaxation of the pressing force of the pressure device (e.g. the loosening of a screw) occurs after a long period of use, the sealing member tends to move toward the opening side. However, this upward movement cannot occur in the present invention since the bottom-side portion of the sealing member, being expanded laterally and fitting with the shape of the wall surface of the cavity, is caught by the wall surface. Therefore, the sealing effect between the sealing member and the bottom of the cavity is maintained even if the pressing force from the pressure device decreases.

BRIEF DESCRIPTION OF THE DRAWINGS

FIG. 1A is a sectional view of the sample injection port before assembly, FIG. 1B is a sectional view in the middle of the assembly, and FIG. 1C is a sectional view after the assembly.

FIG. 3 is a sectional view of a variation of the sample injection port.

FIG. 4 is a sectional view of another variation of the sample injection port.

FIG. 5 is a sectional view of one example of the conventional sample injection ports.

FIG. 6 is a sectional view of another example of the conventional sample injection ports.

BEST MODE FOR CARRYING OUT THE INVENTION

A sealing structure according to one embodiment of the present invention is hereinafter described with reference to the attached drawings. The sealing structure of the present embodiment is used as a part of the sample injection port 10 of an auto-sampler for introducing a sample into a liquid chromatograph.

Figure 1A:
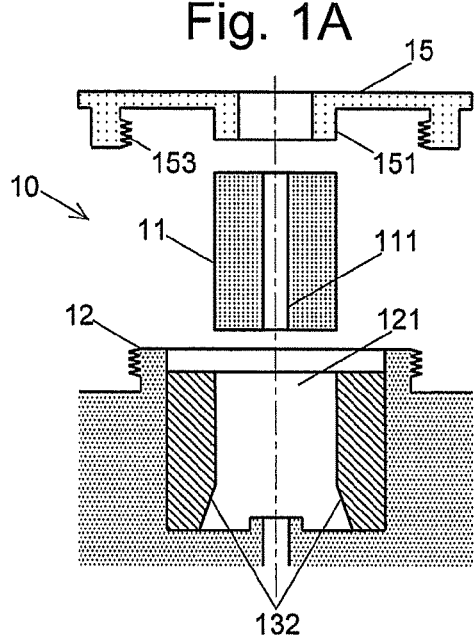
FIGS. 1A-1C are illustrations of a sample injection port having a sealing structure according to one embodiment of the present invention, where
Figure 1B:
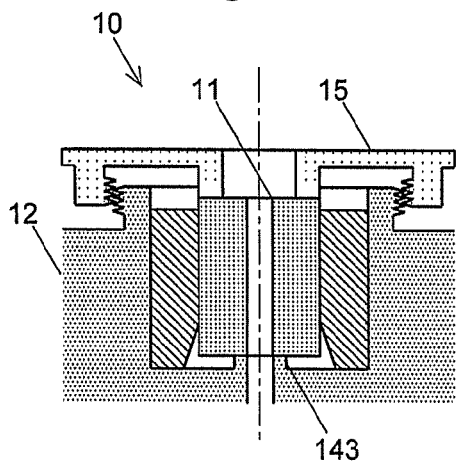
Figure 1C:
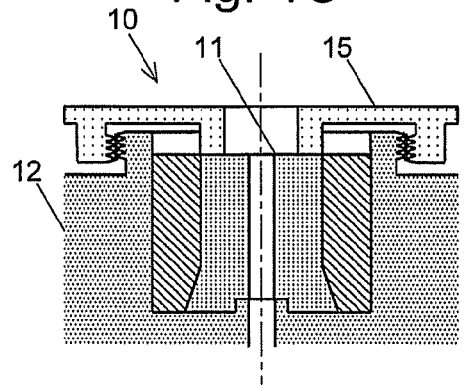

As shown in FIGS. 1A-1C, the sample injection port 10 includes a sealing member 11 having a through-hole 111 for allowing the passage of a liquid sample, a housing 12 having a cavity 121 for holding the sealing member 11, and a cap 15 for pressing the sealing member 11 toward the bottom of the cavity 121.

The sealing member 11 is a resin component having a cylindrical body with the through-hole 111 extending on the central axis thereof. The sealing member 11 used in the present embodiment is a cylindrical part measuring 3 mm in diameter and 10 mm in length, with a through-hole 111 of 0.5 mm in diameter. As for the resin, it is preferable to use a chemical-resistant resin, such as PEEK (polyether ether ketone), PPS (poly phenyl sulfide) or a polyimide, so as to avoid influence on the liquid sample passing through the through-hole 111. Though not shown, the tip of a sampling needle is tightly connected to the upper opening of the through-hole 111.

Figure 2:
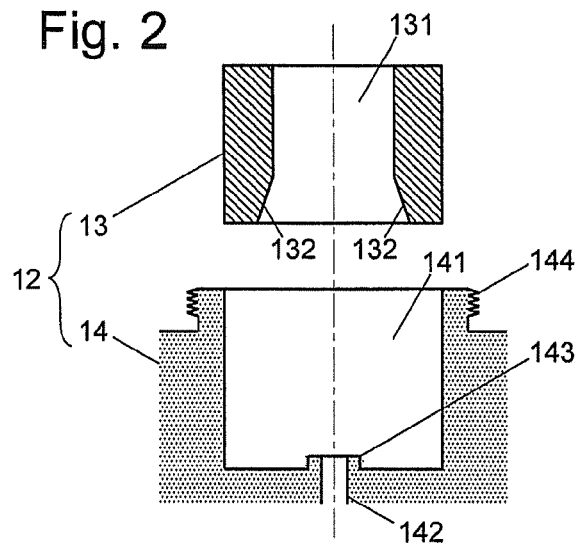
FIG. 2 is an exploded sectional view of a housing.

As shown in FIG. 2, the housing 12 consists of a cylindrical inner housing 13 made of a metal and an outer housing 14 made of a metal with a holding portion 141 for holding the inner housing 13. The inner housing 13 has an insertion hole 131 into which the sealing member 11 is to be placed. The wall surface of the insertion hole 131 is shaped so that its diameter in the portion between the upper end and a predetermined depth (e.g. 7 mm for a 10-mm long inner housing 13) is equal to the outer diameter of the sealing member 11, while its lower portion is in the form of a sloped portion 132 being spread downward. In the present embodiment, the aperture diameter on the lower side of the sloped portion 132, or the aperture diameter at the widest portion thereof, is 3.2 mm. In the outer housing 14, a sample introduction hole 142 having the same diameter as that of the through-hole 111 of the sealing member 11 is formed at the center of the bottom of the holding portion 141. The holding portion 141 may have a flat bottom surface, as shown in FIG. 3. Alternatively, as shown in FIGS. 1A-1C, a ring-shaped projection 143 may be formed around the opening of the sample introduction hole 142 at the bottom of the holding portion 141. The latter design improves the sealing property at the connection part of the passage. The projection 143 in the present embodiment is a ring of 2 mm in outer diameter and 0.5 mm in height. The housing 12 is made of a corrosion resistant metal, such as stainless steel or titanium.

The cap 15 is a roughly disc-shaped metallic part in which a cylindrical pressing portion 151 of the same outer diameter as that of the sealing member 11 protrudes from the central portion of the side directed to the sealing member 11. The inner diameter of the pressing portion 151 is greater than the outer diameter of the sampling needle. A female thread portion 153 protrudes from the circumference of the cap 15 on the side directed to the sealing member 11 (or housing 12). The female thread portion 153 is designed to be engaged with a male thread portion 144 (see FIG. 2) provide around the opening of the holding portion 141 in the outer housing 14.

The process of assembling the sample injection port 10 is as follows: The inner housing 13 is inserted into the holding portion 141 of the outer housing 14 until the lower surface of the inner housing 13 comes in contact with the bottom of the holding portion 141. As a result, a cavity 121 surrounded by the wall surface of the insertion hole 131 of the inner housing 13 and the bottom surface of the holding portion 141 of the outer housing 14 is formed (see FIG. 1A). Then, the sealing member 11 is inserted into this cavity 121 until the lower surface of the sealing member 11 comes in contact with the projection 143 at the bottom of the cavity 121 (see FIG. 1B). In this state, the cap 15 is tightly fastened from above the sealing member 11, whereby a pressure is applied to the upper surface of the sealing member 11 through the pressing portion 151 of the cap 15. Due to this pressure, the lower surface of the sealing member 11 is pressed on the bottom of the cavity 121 and deformed, with the circumferential edge of the bottom of the sealing member 11 being spread in the ring-shaped space formed by the sloped portion 132 (see FIG. 1C). The pressure should preferably be applied to the sealing member 11 to such an extent that the circumferential edge of the bottom of the deformed sealing member 11 fills the ring-shaped space.

The portion of the sealing member 11 closer to its upper surface laterally expands due to the pressure, with its side surface strongly pressed on the wall surface of the cavity 121. This causes a strong friction force at the contact surface, which prevents the pressing force applied from the upper side by the pressing portion 151 from being fully transmitted to the lower side. Accordingly, at the beginning of the pressing operation, the internal stress in the upper portion of the sealing member is higher than that in its lower portion.

With the lapse of time from the beginning of the pressing operation, the upper portion of the sealing member 11 under the higher internal stress gradually moves toward the lower side against the friction force. As a result, the pressure from the upper portion is gradually transmitted to the lower portion, causing an increase in the contact pressure between the sealing member 11 and the housing 12 at the bottom of the cavity. By this mechanism, the sealing property at the connection part of the passage at the bottom is maintained for a long time.

If the connection between the female thread portion 153 and the male thread portion 144 is loosened after a long period of use, the sealing member 11 tends to move toward the upper side. However, this upward movement cannot occur since the lower portion of the sealing member 11, being expanded laterally and fitting with the shape of the wall surface of the cavity 121, is caught by the wall surface. Therefore, the sealing property between the sealing member 11 and the bottom of the cavity 121 is maintained even if the pressing force from the pressing portion 151 decreases.

It is evident that the previous embodiment is one example of the present invention and can be appropriately changed or modified within the spirit of the present invention. For example, as shown in FIG. 4, a step portion 133 extending along the circumference of the lower end of the insertion hole 131 of the inner housing 13 may be provided in place of the sloped portion 132 of the insertion hole 131.

The housing 12 may be made of a resin having a higher modulus of elasticity than the resin used as the material of the sealing member 11. The resin having the higher modulus of elasticity does not need to be a different kind of resin from the one used for the sealing member 11; it is also possible to use a composite material produced by mixing a carbon fiber or similar material in the same resin as used for the sealing member 11 to improve its elastic modulus. The shape of the sealing member 11 is not limited to the cylindrical type; for example, it may be shaped like an elliptic cylinder or prismatic column.

The sealing structure according to the present invention is suitable for the sealing of a connection part of a passage through which a highly pressurized liquid sample is passed. It can be applied to any type of passage connection part other than the sample injection port. Furthermore, it is applicable to not only the passage connection part of an auto-sampler for a liquid chromatograph but also the passage connection parts of other types of analyzing systems.

EXPLANATION OF NUMERALS 10, 50 . . . Sample Injection Port
11, 51 . . . Sealing Member
111, 511 . . . Through-Hole
12, 52 . . . Housing
121 . . . Cavity
13 . . . Inner Housing
131 . . . Insertion Hole
132 . . . Sloped Portion
133 . . . Step Portion
14 . . . Outer Housing
141 . . . Holding Portion
142, 521 . . . Sample Introduction Hole
143, 522 . . . Projection
144 . . . Male Thread Portion
15, 53 . . . Cap
151 . . . Pressing Portion
153 . . . Female Thread Portion

The invention claimed is:

1. A sealing structure, including:
   a) a sealing member having a through-hole for allowing a passage of a sample;
   b) a housing having a cavity for holding the sealing member, the cavity having a sample introduction hole at a bottom thereof, the sample introduction hole communicating with the through-hole; and
   c) a pressure device for pressing the entire sealing member from an opening of the cavity toward the bottom of the cavity,
   wherein the cavity is shaped so that the wall surface of the cavity fits with the external shape of the sealing member in pressure-free state from the opening of the cavity to a predetermined depth thereof while a space is left between the wall surface of the cavity and the external shape of the sealing member in pressure-free state at and around the bottom of the cavity from the aforementioned depth.

2. The sealing structure according to claim 1, wherein
   the sealing member is cylindrical; and
   the cavity has a larger cross section in a portion closer to the bottom thereof from the aforementioned depth than in the portion closer to the opening.

3. The sealing structure according to claim 2, wherein the wall surface of the cavity in the portion closer to the bottom from the predetermined depth is a sloped surface spread toward the bottom.

4. The sealing structure according to claim 1, wherein the sealing member is made of a resin, and the housing is made of a resin having a higher modulus of elasticity than the resin used as a material of the sealing member.

5. The sealing structure according to claim 2, wherein the sealing member is made of a resin, and the housing is made of a resin having a higher modulus of elasticity than the resin used as a material of the sealing member.

6. The sealing structure according to claim 3, wherein the sealing member is made of a resin, and the housing is made of a resin having a higher modulus of elasticity than the resin used as a material of the sealing member.

7. A sealing structure, including:
   a) a sealing member having a through-hole for allowing a passage of a sample;
   b) a housing having a cavity for holding the sealing member, the cavity having a sample introduction hole at a bottom thereof opposite to an opening of the cavity, the sample introduction hole communicating with the through-hole; and
   c) a pressure device for pressing the entire sealing member from an opening of the cavity toward the bottom of the cavity,
   wherein the cavity and the sealing member are shaped such that the external shape of the sealing member fits with the wall surface of the cavity in pressure-free state, except a space is left between the wall surface of the cavity and the external shape of the sealing member in pressure-free state at and around the bottom of the cavity.

8. A sealing structure, including:
a) a sealing member having a through-hole for allowing a passage of a sample;
b) a housing having a cavity for holding the sealing member, the cavity having a sample introduction hole at a bottom thereof, the sample introduction hole communicating with the through-hole, the cavity being larger at and around the bottom of the cavity opposite to an opening of the cavity; and
c) a pressure device for pressing the entire sealing member from an opening of the cavity toward the bottom of the cavity,
wherein the cavity and the sealing member are shaped such that the external shape of the sealing member fits with the wall surface of the cavity in pressure-free state, except a space is left between the wall surface of the cavity and the external shape of the sealing member in pressure-free state at and around the bottom of the cavity.

\* \* \* \* \*